US011272957B2

(12) United States Patent
Stevens

(10) Patent No.: US 11,272,957 B2
(45) Date of Patent: Mar. 15, 2022

(54) COUPLED TORSIONAL FIXATOR AND METHOD OF USE

(71) Applicant: University of Utah Research Foundation, Salt Lake City, UT (US)

(72) Inventor: Peter Stevens, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 239 days.

(21) Appl. No.: 16/588,181

(22) Filed: Sep. 30, 2019

(65) Prior Publication Data

US 2020/0107860 A1    Apr. 9, 2020

Related U.S. Application Data

(60) Provisional application No. 62/741,036, filed on Oct. 4, 2018.

(51) Int. Cl.
*A61B 17/62* (2006.01)
*A61B 17/64* (2006.01)

(52) U.S. Cl.
CPC .......... *A61B 17/62* (2013.01); *A61B 17/6416* (2013.01); *A61M 2210/02* (2013.01)

(58) Field of Classification Search
CPC ............................................ A61B 17/62–6491
See application file for complete search history.

(56) References Cited

U.S. PATENT DOCUMENTS

| | | | |
|---|---|---|---|
| 2,055,024 A | 9/1936 | Bittner, Jr. | |
| 4,033,340 A * | 7/1977 | Kalnberz | A61B 17/62 606/56 |
| 4,365,624 A | 12/1982 | Jaquet | |
| 4,768,524 A | 9/1988 | Hardy | |
| 4,947,835 A | 8/1990 | Hepburn et al. | |
| 5,087,258 A | 2/1992 | Schewior | |
| 5,358,504 A | 10/1994 | Paley et al. | |
| 5,397,322 A | 3/1995 | Campopiano | |

(Continued)

FOREIGN PATENT DOCUMENTS

| | | |
|---|---|---|
| DE | 102015121357 A1 | 6/2017 |
| EP | 1239784 B1 | 4/2006 |

(Continued)

OTHER PUBLICATIONS

International Search Report dated Jan. 9, 2020 for corresponding PCT Application No. PCT/US2019/053907.

*Primary Examiner* — Nicholas J Plionis
(74) *Attorney, Agent, or Firm* — David Meibos; Maywood IP Law

(57) ABSTRACT

An apparatus and method for external anteversion correction of an intact bone may include a first arcuate segment, a second arcuate segment rotatably coupled to the first arcuate segment, a first pin extending from the first arcuate segment to a proximal segment of the intact bone, a second pin extending from the second arcuate segment to a distal segment of the intact bone, and a control mechanism attached to the first and second arcuate segments. The control mechanism may rotate the first arcuate segment relative to the second arcuate segment to exert torsional force on the intact bone between the proximal and distal segments of the intact bone, thereby externally reducing anteversion of the intact bone.

7 Claims, 16 Drawing Sheets

(56) References Cited

U.S. PATENT DOCUMENTS

| | | |
|---|---|---|
| 5,630,814 A | 5/1997 | Ross, Jr. et al. |
| 5,728,095 A | 3/1998 | Taylor et al. |
| 5,971,984 A | 10/1999 | Taylor et al. |
| 5,997,537 A | 12/1999 | Walulik |
| 6,017,341 A | 1/2000 | Windhagen et al. |
| 6,030,386 A | 2/2000 | Taylor et al. |
| 6,102,911 A | 8/2000 | Faccioli et al. |
| 6,860,883 B2 | 3/2005 | Janowski et al. |
| 7,226,449 B2 | 6/2007 | Venturini et al. |
| 7,361,176 B2 | 4/2008 | Cooper et al. |
| 8,202,273 B2 | 6/2012 | Karidis |
| 8,430,878 B2 | 4/2013 | Vasta et al. |
| 8,491,599 B2 | 7/2013 | Heilala et al. |
| 8,679,117 B2 | 3/2014 | Knuchel et al. |
| 8,814,866 B2 | 8/2014 | Vaidya |
| 8,864,763 B2 | 10/2014 | Murray et al. |
| 8,951,252 B2 | 2/2015 | Steiner et al. |
| 9,011,438 B2 | 4/2015 | Steiner et al. |
| 9,023,045 B2 | 5/2015 | Lehmann et al. |
| 9,044,271 B2 | 6/2015 | Edelhauser et al. |
| 9,101,398 B2 | 8/2015 | Singh et al. |
| 9,289,238 B2 | 3/2016 | Ross et al. |
| 9,308,025 B2 | 4/2016 | Zgonis et al. |
| 9,445,841 B2 | 9/2016 | Samchukov et al. |
| 9,757,153 B2 | 9/2017 | Jay et al. |
| 9,808,288 B2 | 11/2017 | Wong et al. |
| 10,076,375 B1 | 9/2018 | Martel |
| 2003/0106230 A1 | 6/2003 | Hennessey |
| 2003/0153910 A1 | 8/2003 | Janowski et al. |
| 2005/0043730 A1 | 2/2005 | Janowski et al. |
| 2006/0184169 A1 | 8/2006 | Stevens |
| 2007/0055233 A1* | 3/2007 | Brinker .......... A61B 17/66 606/54 |
| 2008/0269741 A1 | 10/2008 | Karidis |
| 2009/0036890 A1 | 2/2009 | Karidis |
| 2009/0264884 A1 | 10/2009 | Masse et al. |
| 2009/0287212 A1* | 11/2009 | Hirata .......... A61B 17/6466 606/59 |
| 2010/0191239 A1 | 7/2010 | Sakkers et al. |
| 2011/0118738 A1 | 5/2011 | Vasta et al. |
| 2011/0313419 A1 | 12/2011 | Mullaney |
| 2012/0303029 A1 | 11/2012 | Vasta et al. |
| 2015/0216565 A1* | 8/2015 | Paley .......... A61B 17/68 606/328 |
| 2015/0257803 A1* | 9/2015 | Sampath .......... A61B 17/8004 606/71 |
| 2016/0022314 A1 | 1/2016 | Bordeaux et al. |
| 2016/0066956 A1 | 3/2016 | Siemer et al. |
| 2017/0354439 A1 | 12/2017 | Mannanal et al. |
| 2018/0042651 A1* | 2/2018 | Little .......... A61B 17/7216 |
| 2020/0275953 A1* | 9/2020 | Park .......... A61B 17/66 |

FOREIGN PATENT DOCUMENTS

| | | | |
|---|---|---|---|
| KR | 1015016350000 | 3/2015 | |
| WO | WO2007075114 | 7/2007 | |
| WO | WO-2020178343 A1 * | 9/2020 | .......... A61B 17/66 |

* cited by examiner

COUPLED TORSIONAL FIXATOR AND METHOD OF USE

CROSS-REFERENCE TO RELATED APPLICATIONS

This application claims the benefit of U.S. Provisional Patent Application Ser. No. 62/741,036 entitled "COUPLED TORSIONAL FIXATOR AND METHOD OF USE," which was filed on Oct. 4, 2018, the disclosure of which is incorporated herein by reference in its entirety.

TECHNICAL FIELD

The present disclosure relates to medical devices, systems, and methods. More specifically, the present disclosure relates to improved medical devices, systems, and methods for external anteversion correction of intact bones.

BACKGROUND

In normal human development, the femur is characterized by about 11° of forward inclination of the upper femur (e.g., the neck and head of the femur) relative to the lower end of the femur (e.g., the shaft and femoral condyles). FIG. 1A illustrates an inferior view of a femur with normal anatomy, enabling proper gait with the foot facing forward.

In contrast to normal femoral development, femoral anteversion is characterized by excessive forward inclination of the upper femur relative to the lower femur, as illustrated in FIG. 1B, which illustrates a femur with 30 degrees of anteversion. Femoral anteversion results in a knee that twists inward relative to the hip, which results in "intoeing" of the foot. This may predispose a patient to hip injuries (e.g., labrum injuries, etc.) and knee injuries (e.g., patellar injuries, ACL injuries, etc.). Persistent torsional deformity due to anteversion cannot be corrected with a brace or with physical therapy.

One remedy for anteversion includes performing a rotational osteotomy of the femur. This typically requires internal fixation with a large plate or intramedullary rod that is usually removed once the bone has healed after the procedure. During a traditional correction procedure for femoral anteversion, called a femoral derotation osteotomy, the surgeon cuts the femur, rotates the ball of the femur in the hip socket to a normal position, and then reattaches the resected bone portions together. A large plate or intramedullary rod is then implanted to hold the resected bone portions in a corrected orientation. However, this surgery is extremely invasive and associated with many negative features and risks. Some of the negative items associated with this procedure include: (1) significant surgical scarring; (2) over/under-correction of the anteversion; (3) significant pain; (4) delayed walking after the procedure; (5) possible loss of fixation; (6) delayed healing; (7) non-union of the bone; (8) time/costs associated with inpatient procedures, etc. Accordingly, improved medical devices, systems, and methods that can alleviate some, or all, of these negative features would be desirable.

SUMMARY

The various medical devices, systems, and methods of the present disclosure have been developed in response to the present state of the art, and in particular, in response to the problems and needs in the art that have not yet been fully solved by currently available medical devices, systems, and methods for correcting bone anteversion.

According to some embodiments, a device for external femoral anteversion correction of an intact femur comprising a distal femoral segment and a proximal femoral segment on opposing sides of a physis may generally include a coupled ring assembly, a first fixation pin assembly, a second fixation pin assembly, and a turnbuckle assembly. The coupled ring assembly may include an outer ring assembly and an inner ring element. The outer ring assembly may include a first outer ring element and a second outer ring element configured to couple with the first outer ring element to form the outer ring assembly. The inner ring element may be configured to concentrically and rotatably couple with the outer ring assembly. The first fixation pin assembly may include a first pin securable to the distal femoral segment and a first coupler configured to couple with the outer ring assembly and the first pin. The second fixation pin assembly may include a second pin securable to the proximal femoral segment and a second coupler configured to couple with the inner ring element and the second pin. The turnbuckle assembly may include a first fixation element configured to couple with the outer ring assembly, a second fixation element configured to couple with the inner ring element, and a spanning element configured to rotatably couple with the first fixation element and the second fixation element. Rotation of the spanning element may: (1) cause the outer ring assembly to rotate relative to the inner ring element; (2) control an angular position of the first pin with respect to the second pin; and (3) impart a torsional force to the intact femur to externally reduce anteversion of the intact femur.

In some embodiments of the device, the outer ring assembly may include a plurality of columnar passageways and the inner ring element may include a plurality of apertures. The plurality of columnar passageways may be configured to receive a first fastener configured to couple the first fixation pin assembly to the outer ring assembly. The plurality of apertures may be configured to receive a second fastener configured to couple the second fixation pin assembly to the inner ring element. The plurality of columnar passageways may be configured to receive the first fixation element to pivotably couple the turnbuckle assembly with the outer ring assembly, and the plurality of apertures may also be configured to receive the second fixation element to pivotably couple the turnbuckle assembly with the inner ring element.

In some embodiments of the device, at least one of the first pin and the second pin may include one or more wires secured between two opposing couplers that are positioned on opposite sides of the coupled ring assembly.

In some embodiments of the device, one of the outer ring assembly and the inner ring element may include a plurality of indicia configured to indicate a range of anteversion correction, and the other one of the outer ring assembly and the inner ring element may include a pointer configured to indicate a selected amount of anteversion correction with reference to the range of anteversion correction that is indicated by the plurality of indicia.

In some embodiments of the device, the first fixation element of the turnbuckle assembly may include first threading and the second fixation element of the turnbuckle assembly may include second threading. The spanning element of the turnbuckle assembly may include third threading configured to engage the first threading of the first fixation element and fourth threading configured to engage the second threading of the second fixation element. In this manner, rotating the spanning element in a first direction may cause the first and second fixation elements to move away from each other, and rotating the spanning element in a second direction may cause the first and second fixation elements to move toward each other.

In some embodiments of the device, the first outer ring element may include a first notch and the second outer ring element may include a second notch. The inner ring element may include a circular flange that may concentrically fit within the first and second notches when the first and second outer ring elements are assembled together to form the outer ring assembly.

In other embodiments, an apparatus configured to apply an external torsion force to an intact bone may include a first arcuate segment, a second arcuate segment rotatably coupled to the first arcuate segment, a first pin extending from the first arcuate segment to a proximal segment of the intact bone, a second pin extending from the second arcuate segment to a distal segment of the intact bone, and a control mechanism attached to the first arcuate segment and to the second arcuate segment. The control mechanism may enable fixation of the second arcuate segment in any of a plurality of orientations relative to the first arcuate segment in order to control an orientation of the first pin with respect to the second pin to exert torsional force on the intact bone between the proximal segment and the distal segment, thereby externally reducing anteversion of the intact bone.

In some embodiments of the apparatus, the first arcuate segment may include an outer ring and the second arcuate segment may include an inner ring concentrically and rotatably coupled to the outer ring. The apparatus may also include a first pin fixation assembly attached to the outer ring, with the first pin extending from the first pin fixation assembly, and a second pin fixation assembly attached to the inner ring, with the second pin extending from the second pin fixation assembly.

In some embodiments of the apparatus, the control mechanism may include a turnbuckle assembly having a first fixation element configured to couple with the outer ring, a second fixation element configured to couple with the inner ring, and a spanning element configured to rotatably couple with the first fixation element and the second fixation element. Rotation of the spanning element may: (1) cause the outer ring to rotate relative to the inner ring; (2) control an angular position of the first pin with respect to the second pin; and (3) impart a torsional force to the intact bone to externally reduce anteversion of the intact bone.

In some embodiments of the apparatus, the first fixation element of the turnbuckle assembly may include first threading and the second fixation element of the turnbuckle assembly may include second threading. The spanning element of the turnbuckle assembly may include third threading configured to engage the first threading of the first fixation element, and fourth threading configured to engage the second threading of the second fixation element. Rotating the spanning element in a first direction may cause the first and second fixation elements to move away from each other, and rotating the spanning element in a second direction may cause the first and second fixation elements to move toward each other.

In some embodiments of the apparatus, one of the outer ring and the inner ring may include a plurality of indicia configured to indicate a range of anteversion correction, and the other one of the outer ring and the inner ring may include a pointer configured to indicate a selected amount of anteversion correction with reference to the range of anteversion correction indicated by the plurality of indicia.

In some embodiments of the apparatus, the outer ring may include a first outer ring element and a second outer ring element configured to couple with the first outer ring element to form the outer ring.

In some embodiments of the apparatus, the first outer ring element may include a first notch, the second outer ring element may include a second notch, and the inner ring may include a circular flange. The circular flange of the inner ring may concentrically fit within the first and second notches when the first and second outer ring elements are assembled together to form the outer ring.

In yet other embodiments, a method for external anteversion correction of an intact bone (through use of a device comprising a first arcuate segment and a second arcuate segment rotatably coupled together, a first pin coupled to the first arcuate segment, a second pin coupled to the second arcuate segment, and a control mechanism coupled to the first and second arcuate segments), may include percutaneously securing the first pin to a distal bone segment of the intact bone, and percutaneously securing the second pin to a proximal bone segment of the intact bone at a selected first angle relative to the first pin. The method may also include actuating the control mechanism, thereby: rotating the first arcuate segment relative to the second arcuate segment; moving the second pin to a selected second angle relative to the first pin; and twisting the proximal bone segment relative to the distal bone segment to reduce anteversion of the intact bone.

In some embodiments of the method, the first arcuate segment may include an outer ring and the second arcuate segment may include an inner ring concentrically and rotatably coupled to the outer ring.

In some embodiments of the method, actuating the control mechanism may further include incrementally actuating the control mechanism over a period of time, thereby: rotating the inner ring relative to the outer ring to a plurality of different positions; moving the second pin to a plurality of different angles relative to the first pin; and gradually twisting the proximal bone segment relative to the distal bone segment to reduce anteversion of the intact bone over the period of time.

In some embodiments, the method may also include removing the first and second pins from the intact bone when a desired anteversion correction of the intact bone is reached.

In some embodiments of the method, actuating the control mechanism may include rotating at least a portion of the control mechanism, thereby: increasing a length of the control mechanism; rotating the inner ring relative to the outer ring; moving the second pin to a selected second angle relative to the first pin; and twisting the proximal bone segment relative to the distal bone segment to reduce anteversion of the intact bone.

In some embodiments of the method, rotating the at least a portion of the control mechanism in a first direction may increase the length of the control mechanism, and rotating the at least a portion of the control mechanism in a second direction may decrease the length of the control mechanism.

In some embodiments of the method, the control mechanism may include a turnbuckle assembly having a first fixation element configured to pivotally couple with the outer ring, a second fixation element configured to pivotally couple with the inner ring, and a spanning element configured to rotatably couple with the first fixation element and the second fixation element. Actuating the control mechanism may include rotating the spanning element, thereby: increasing a length of the control mechanism; rotating the inner ring relative to the outer ring; moving the second pin to a selected second angle relative to the first pin; and twisting the proximal bone segment relative to the distal bone segment to reduce anteversion of the intact bone.

These and other features and advantages of the present disclosure will become more fully apparent from the following description and appended claims, or may be learned by the practice of the devices, systems, and methods set forth hereinafter.

BRIEF DESCRIPTION OF THE DRAWINGS

Exemplary embodiments of the present disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

Figure 1A:
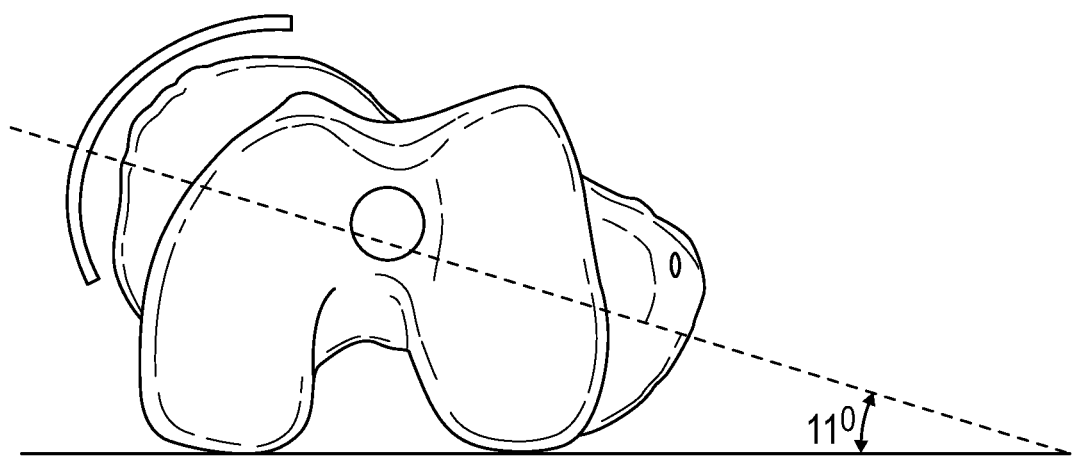
FIG. 1A is an inferior view of a normal femur.
Figure 1B:
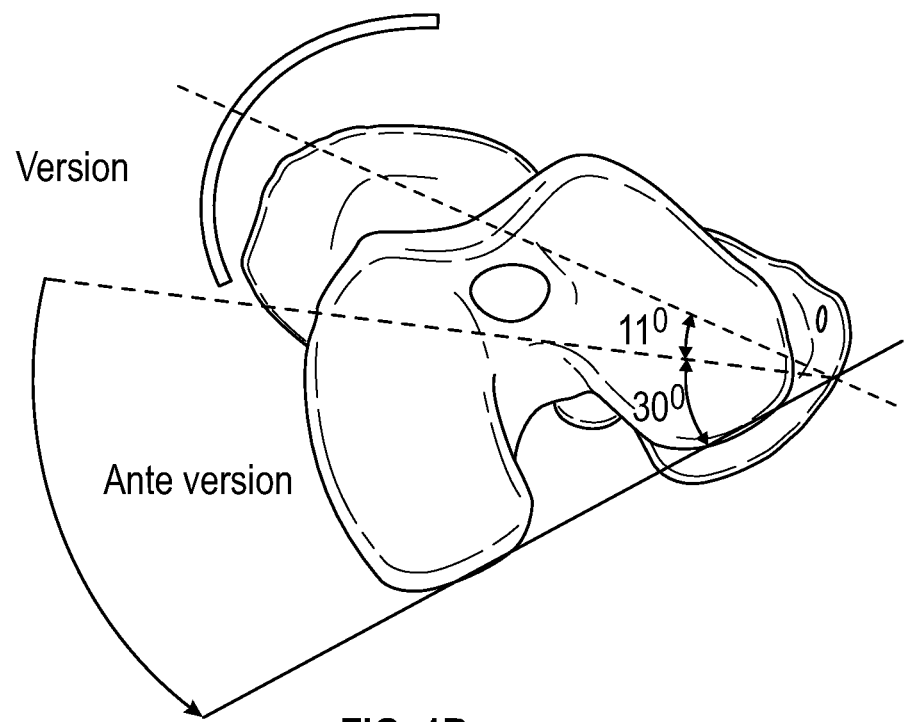
FIG. 1B is an inferior view of a femur with 30 degrees of anteversion.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus, system, and method, as represented in FIGS. 2-14, is not intended to limit the scope of the present disclosure, as claimed in this or any other application claiming priority to this application, but is merely representative exemplary of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Disclosed herein are devices and methods for anteversion correction which are less invasive and can provide quicker/more reliable correction of torsional deformities than traditional correction procedures. Advantages of using the coupled torsional fixators disclosed herein over femoral derotation osteotomies may include: (1) ease of removal (e.g., removal of an external frame vs. removal of an internal plate or IM rod); (2) outpatient procedure vs. inpatient procedure; (3) minimal scarring (e.g., at the pin sites); (4) adjustability; (5) reduced pain; (6) immediate ability to walk following the procedure; (7) secure fixation; and (8) no bone healing is required. Full weight bearing is possible following the correction procedure disclosed herein, since the bone remains intact.

Although the present disclosure illustrates anteversion correction with reference to femoral bones, it will also be understood that the devices, systems, and methods disclosed herein may also be with other types of bones to correct abnormal torsional alignment. For example, the devices, systems, and methods disclosed herein may be utilized to untwist an upper tibia in patients with inward or outward tibial torsion, etc.

FIGS. 2-5 illustrate a coupled torsional fixator 100, as one non-limiting example of an anteversion correction device of the present disclosure for external femoral anteversion correction of an intact bone. The coupled torsional fixator 100 may generally include a coupled ring assembly 102, a control mechanism or turnbuckle assembly 104, a first fixation pin assembly 106, and a second fixation pin assembly 108.

In use, the first and second fixation pin assemblies 106, 108 may be percutaneously affixed to a patient's intact bone, such as an intact femur comprising a distal femoral segment and a proximal femoral segment on opposing sides of a physis or physeal growth plate of the intact femur. The turnbuckle assembly 104 may then be adjusted to provide and maintain a corrective torsional force between the first and second fixation pin assemblies 106, 108. The amount of corrective torsional force between the first and second fixation pin assemblies 106, 108 can be gradually adjusted until a partial or complete anteversion correction has been achieved.

As shown in FIGS. 2-6B, the coupled ring assembly 102 may include an outer ring assembly 103 comprising a first outer ring element 120 and a second outer ring element 122 configured to couple with each other, as well as an inner ring element 124 which may be concentrically nested between the first and second outer ring elements 120, 122 and may rotatably couple with the first and second outer ring elements 120, 122. A ring assembly bore 126 may be defined by the inner surface of inner ring element 124. A fixator central axis 101 may extend through the center of ring assembly bore 126.

In at least one embodiment, the first and second outer ring elements 120, 122 may be identical, differing only in their relative orientations when operatively assembled with the inner ring element 124 to form the coupled ring assembly 102. Accordingly, the first outer ring element 120 is described below with the understanding that this description may also apply to the second outer ring element 122.

Figure 6A:
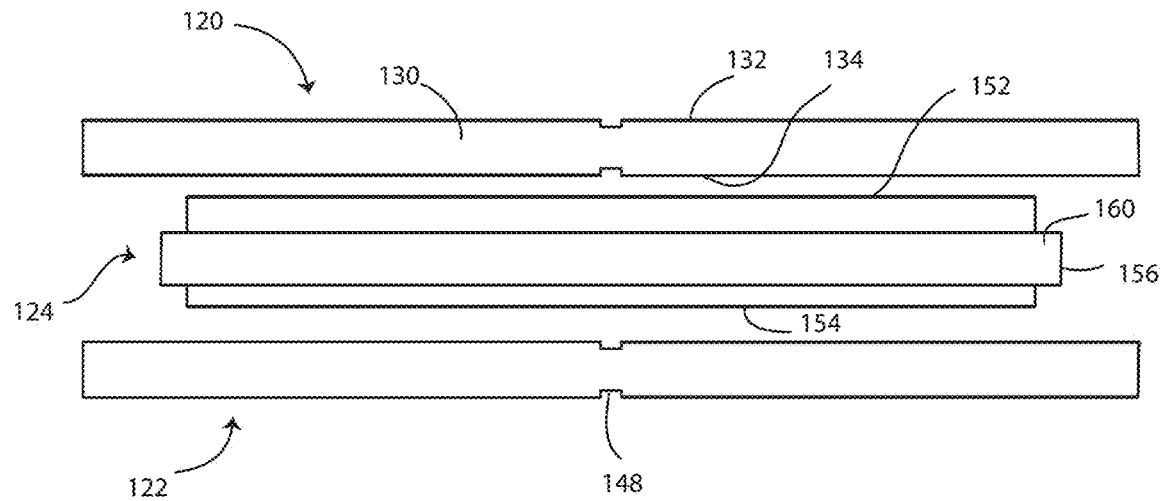
FIG. 6A is an exploded view of a coupled ring assembly of the anteversion correction device of FIG. 2.
Figure 6B:
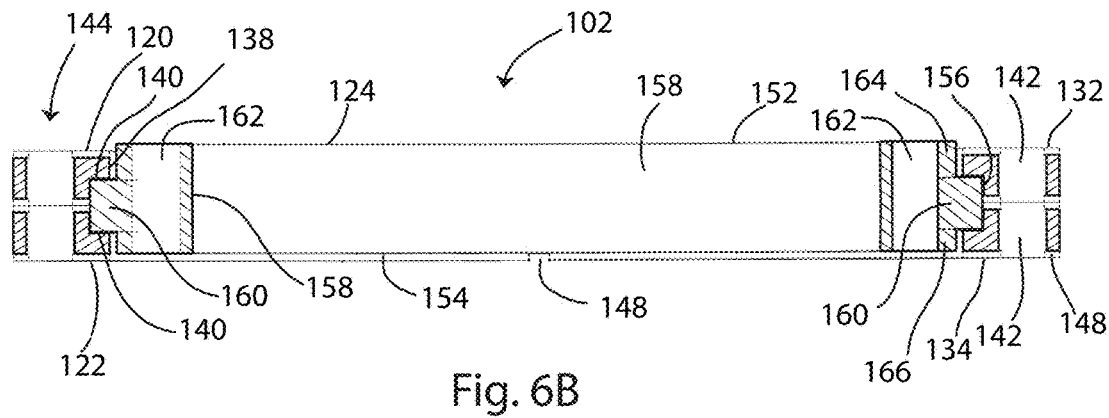
FIG. 6B is a cross-sectional view of the coupled ring assembly.
Figure 7:
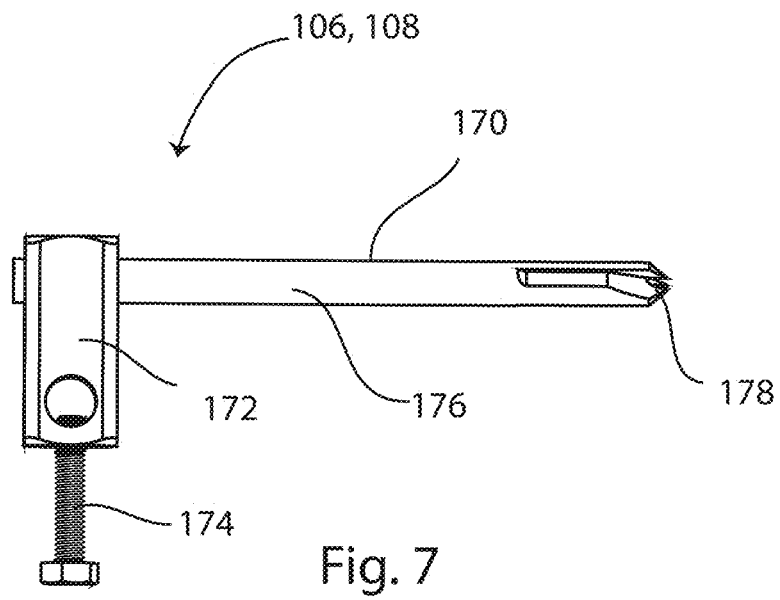
FIG. 7 is a side view of an example pin assembly of the anteversion correction device of FIG. 2.
Figure 8:
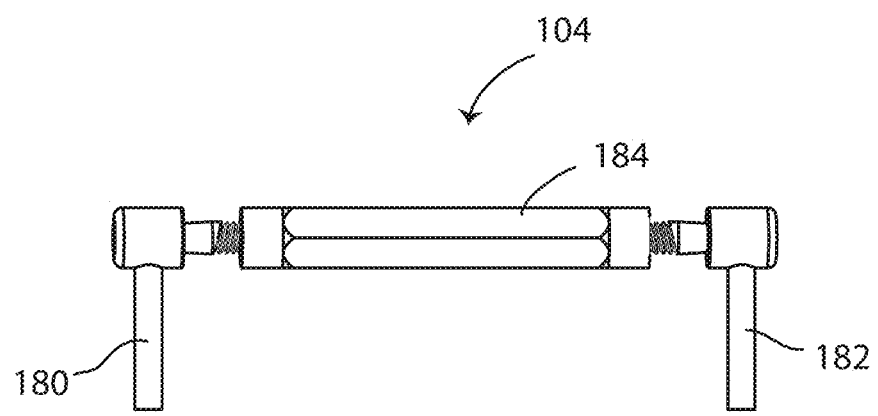
FIG. 8 is a side view of an example turnbuckle assembly of the anteversion correction device of FIG. 2.

In at least one embodiment, the first outer ring element 120 may comprise an outer ring body 130 formed as a complete circle, having a superior surface 132, an inferior surface 134, an outer surface 136, and an inner surface 138, as is best seen in FIG. 6B. The inner surface 138 may include a step or notch 140, into which the inner ring element 124 may concentrically fit.

Figure 10:
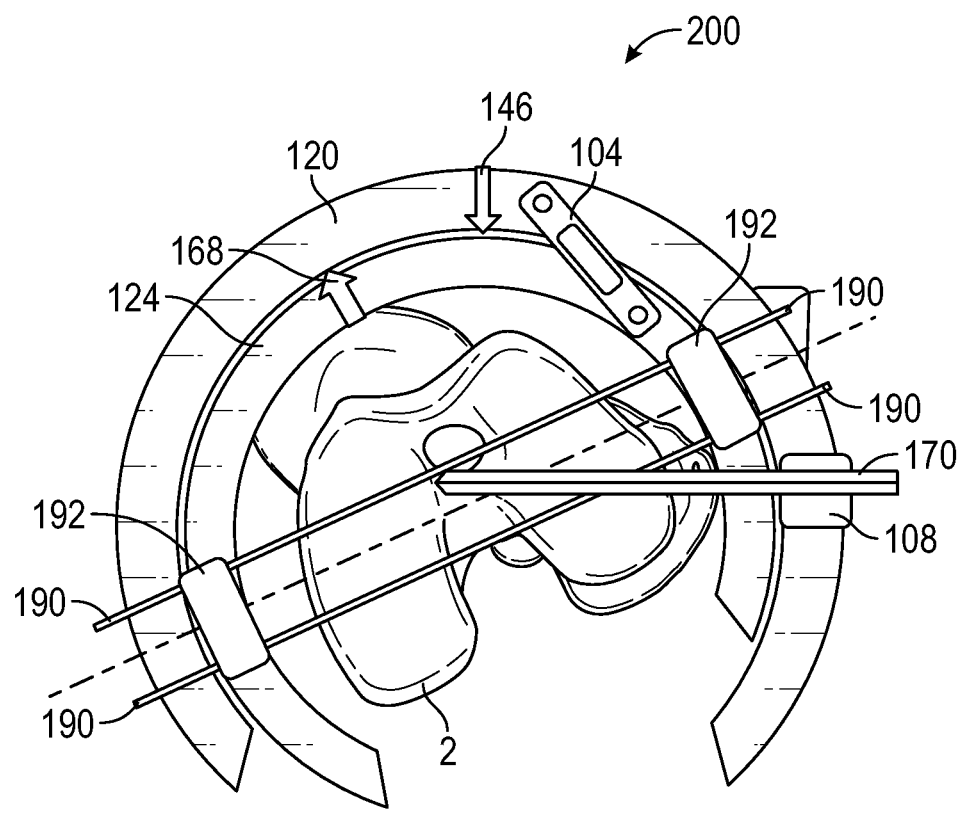
FIG. 10 is an inferior view of a femur with an alternate embodiment of an anteversion correction device affixed to the femur, before correction of anteversion in the femur.
Figure 11:
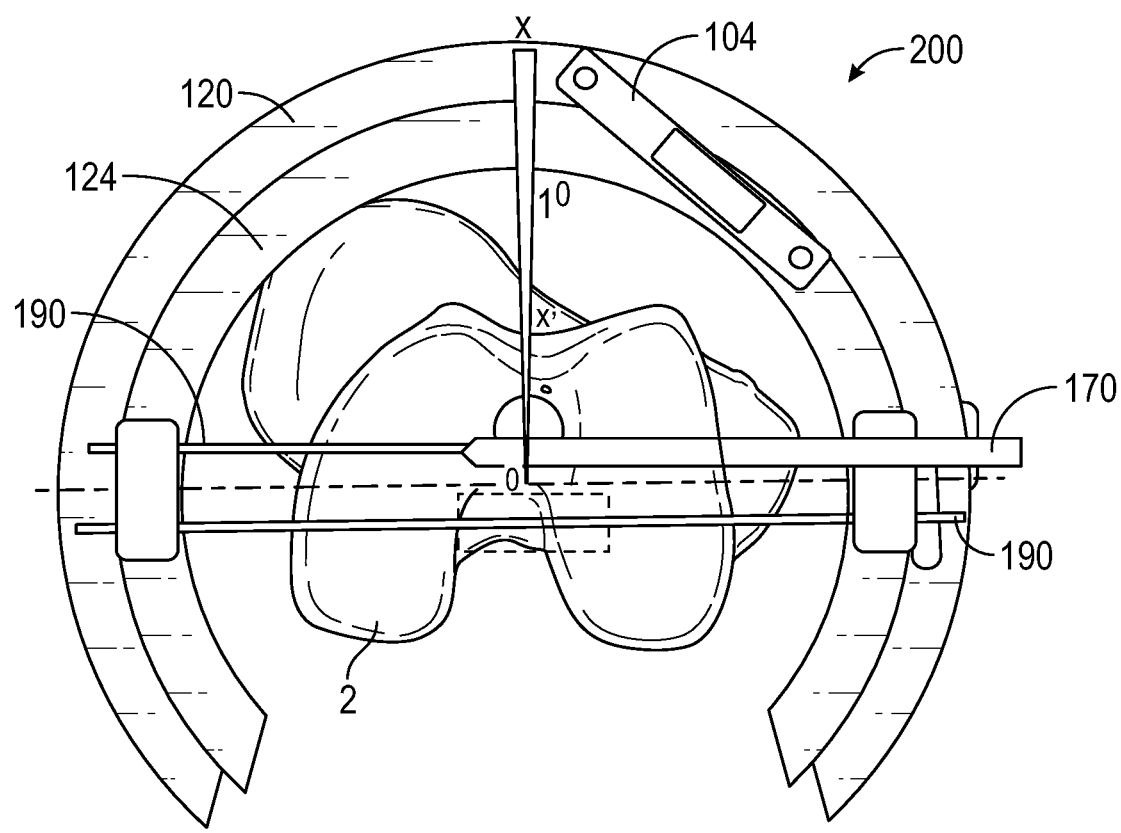
FIG. 11 is an inferior view of the femur and the anteversion correction device of FIG. 10, during correction of anteversion in the femur.

However, it will also be understood that in other embodiments the first outer ring element 120 may comprise a first arcuate segment and the inner ring element 124 may comprise a second arcuate segment, each of which may not form complete circles (e.g., see FIGS. 10 and 11). These first and second arcuate segments may be rotatably coupled to each other, in like fashion.

As shown in FIG. 6B, a plurality of outer ring apertures 142 may extend between the superior and inferior surfaces 132, 134, for receiving the first fixation pin assembly 106 and/or at least a portion of the turnbuckle assembly 104. When the first and second outer ring elements 120, 122 are operatively oriented with respect to one another, as shown in FIGS. 2, 3, 4, and 6B, the outer ring apertures 142 formed in the first and second outer ring elements 120, 122 may vertically align with each other to form a plurality of columnar passageways 144 extending through the outer ring apertures 142 formed in the first and second outer ring elements 120, 122. The plurality of columnar passageways 144 may be configured to receive a first fastener (such as the bolt 174 shown in FIG. 7), which may be configured to couple the first fixation pin assembly 106 to the outer ring assembly 103. The plurality of columnar passageways 144 may also be configured to receive a first fixation element 180 of the turnbuckle assembly 104 in order to pivotably couple of the turnbuckle assembly 104 with the outer ring assembly 103, as will be discussed in more detail below.

The first and second outer ring elements 120, 122 (and/or the inner ring element 124) may include indicia 146 which may denote degrees indicative of a range of anteversion correction, such that the anteversion correction can be accurately prescribed, executed, and/or tracked. The indicia 146 may include a central point, or zero degree indicator 147. The first and second outer ring elements 120, 122 may also include one or more grooves 148 or other features to assist in correctly orienting the first and second outer ring elements 120, 122 with respect to one another.

In at least one embodiment, the inner ring element 124 may comprise an inner ring body 150 formed as a complete circle and having a superior surface 152, an inferior surface 154, an outer surface 156, and an inner surface 158. A circular flange 160 may protrude outwardly from the inner ring body 150. The circular flange 160 may be received between the notches 140 formed in the first and second outer ring elements 120, 122 in order to concentrically nest the inner ring element 124 between the first and second outer ring elements 120, 122.

As shown in FIG. 6B, a plurality of inner ring apertures 162 may extend between the superior and inferior surfaces 152, 154 of the inner ring element 124. The plurality of inner ring apertures 162 may be configured to receive a second fastener (such as the bolt 174 shown in FIG. 7), which may be configured to couple the second fixation pin assembly 108 to the inner ring element 124. The plurality of inner ring apertures 162 may also be configured to receive a second fixation element 182 of the turnbuckle assembly 104 in order to pivotably couple the turnbuckle assembly 104 with the inner ring element 124.

In at least one embodiment, the height of the inner ring element 124 between its superior and inferior surfaces 152, 154 may be equal to, or substantially equal to, the combined heights of the first and second outer ring elements 120, 122.

Figure 3:
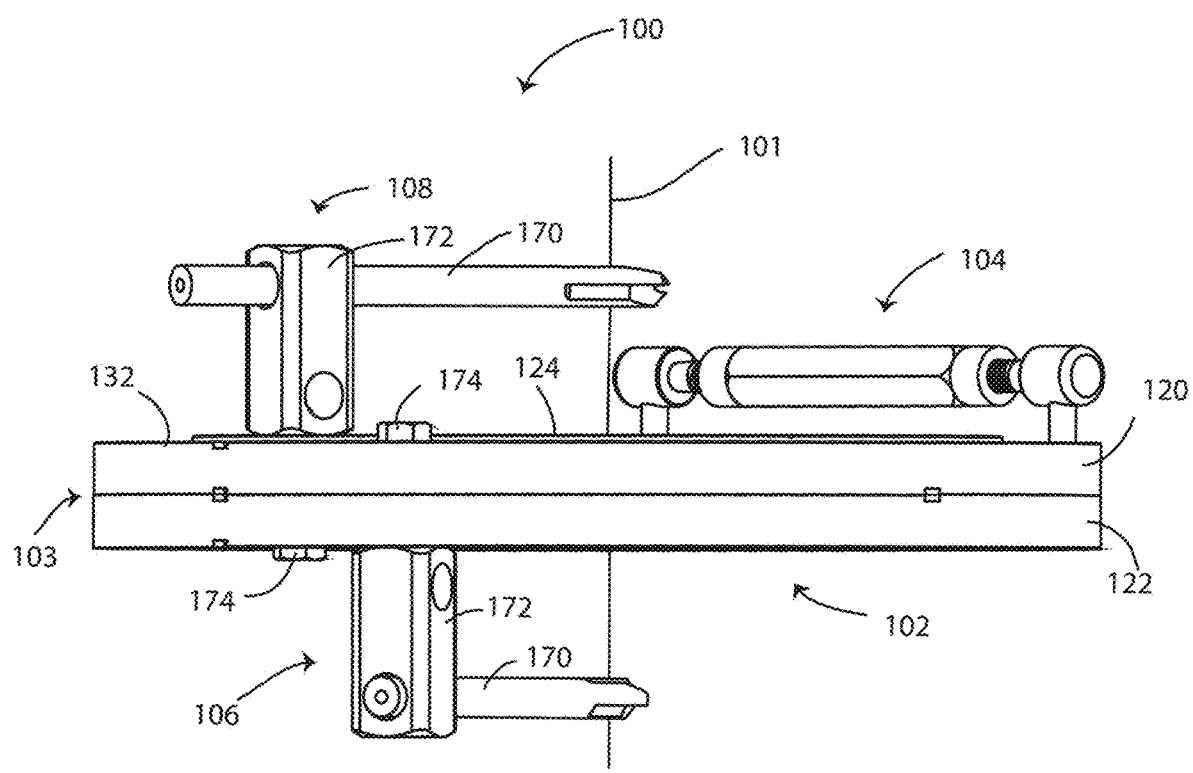
FIG. 3 is a side view of the anteversion correction device of FIG. 2.

In at least one embodiment, a superior portion 164 of the inner ring body 150 (e.g., above the circular flange 160) may be greater in height than an inferior portion 166 of the inner ring body 150 (e.g., below the circular flange 160), as shown in FIG. 6B. Thus, as can be seen in FIGS. 3 and 6B, a portion of the inner ring element 124 may protrude above the superior surface 132 of the first outer ring element 120 when the coupled ring assembly 102 is operatively assembled together. Likewise, in this embodiment, the inferior surface 154 of the inner ring element 124 may be slightly recessed from the inferior surface of the second outer ring element 122. This height difference between the outer and inner ring elements may assist in manipulating the coupled torsional fixator 100.

When operatively assembled, as shown in FIGS. 2-5, the inner ring element 124 may be rotatable with respect to the first and second outer ring elements 120, 122, about the fixator central axis 101. A pointer 168, or another indicator, may also be present on either or both of the superior and inferior surfaces 152, 154 of the inner ring element 124 (and/or on either or both of the first and second outer ring elements 120, 122) in order to help facilitate prescribing, measuring, and tracking anteversion correction.

Referring to FIGS. 2-5 and 7, each of the first and second fixation pin assemblies 106, 108 may generally comprise a pin 170, a coupler 172, and a fastener or bolt 174, in at least one embodiment. The pin 170 may include a shaft 176 and a point 178 for percutaneous fixation in the patient's femur. In at least some embodiments, the pin 170 may be cannulated and/or self-tapping. It will be understood that the point 178 may comprise any suitable form known in the art for penetrating and affixing within a bone, including, but not limited to: flutes, facets, sharpened points, serrations, and other penetrating elements that are known the art. Similarly, the pin 170 may comprise a wire, screw, nail, post, rod, rigid cable, or other longitudinally extending rigid element. The coupler 172 may include at least one passage (not shown in FIG. 7) for receiving the shaft 176, and a threaded opening (not shown in FIG. 7) for receiving the bolt 174. In at least one embodiment, the pin 170 and the coupler 172 may be separate members which may be coupled together. However, in other embodiments, the pin 170 and the coupler 172 may comprise a single monolithic body.

Figure 4:
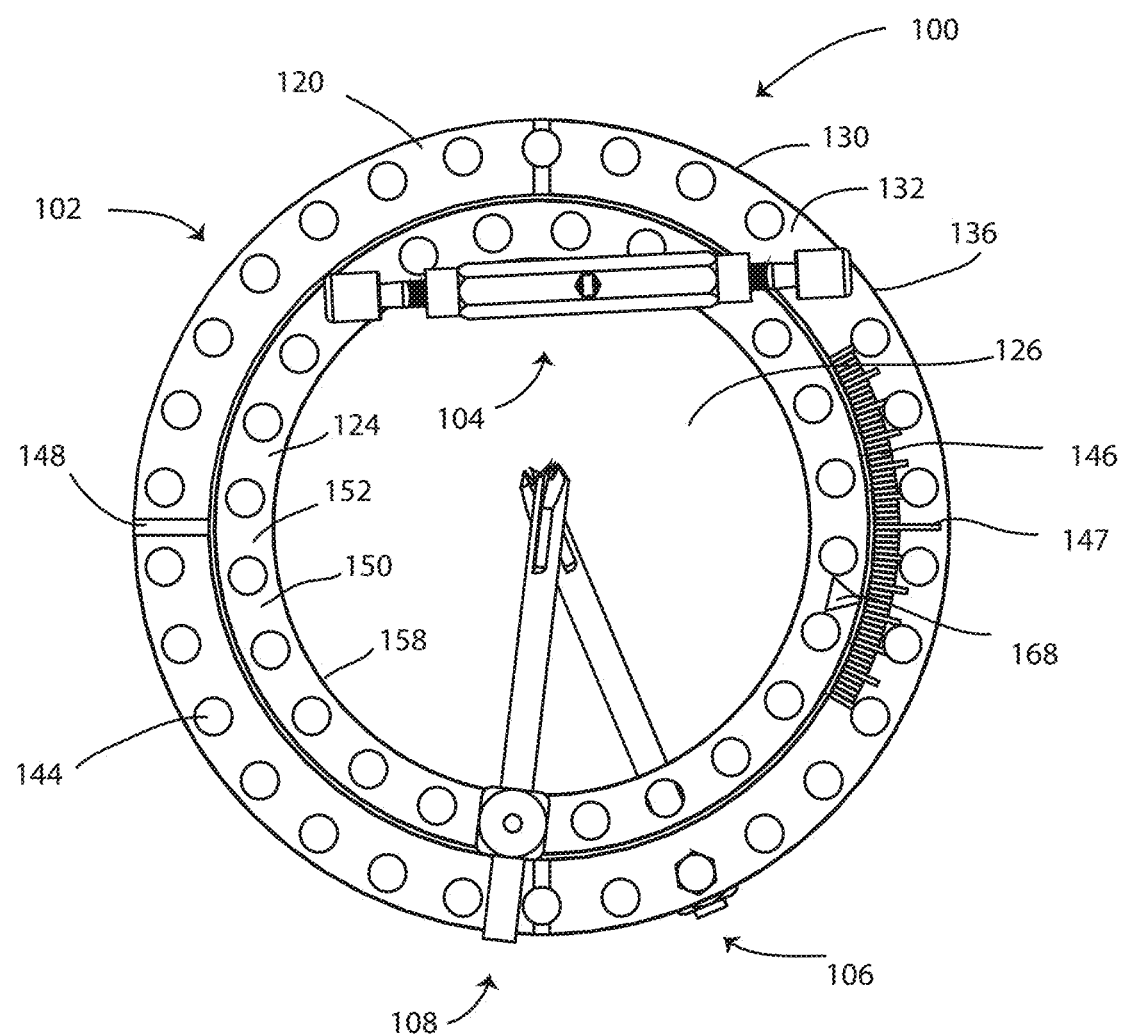
FIG. 4 is a superior view of the anteversion correction device of FIG. 2.
Figure 5:
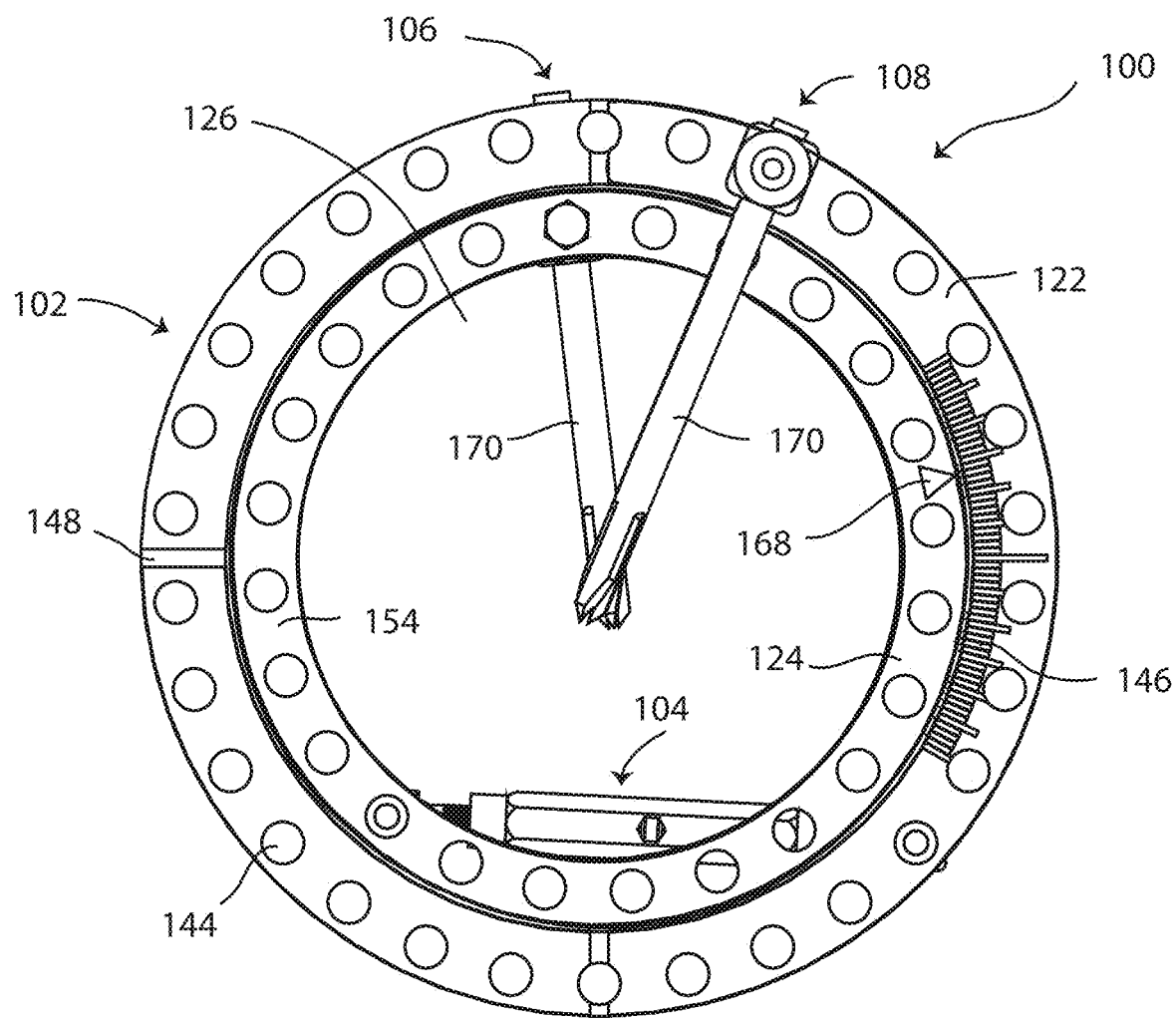
FIG. 5 is an inferior view of the anteversion correction device of FIG. 2.

The first fixation pin assembly 106 may be coupled to the first and/or second outer ring elements 120, 122 via the bolt 174 passing through one of the columnar passageways 144 formed through the first and second outer ring elements 120, 122 (e.g., see FIG. 3). The first fixation pin assembly 106 may project inferiorly from the second outer ring element 122. Likewise, the second fixation pin assembly 108 may be coupled to the inner ring element 124 via the bolt 174 passing through one of the inner ring apertures 162 formed in the inner ring element 124. The second fixation pin assembly 108 may project superiorly from the first outer ring element 120. Both pins 170 of the first and second fixation pin assemblies 106, 108 may project inwardly relative to the outer surface 136 of the second outer ring element 122, as shown in FIGS. 4 and 5. Moreover, both pins 170 of the first and second fixation pin assemblies 106, 108 may assume any angular position with respect to each other as the outer ring assembly 103 rotates relative to the inner ring element 124.

In at least one embodiment, the coupled torsion fixator 100 may include two fixation pin assemblies. However, in other embodiments (not shown) fewer or more fixation pin assemblies may be utilized. In addition, it will be understood that the relative placement of the pin assemblies on the inner and outer rings may vary without departing from the spirit or scope of the present disclosure.

Referring to FIGS. 2-5 and 8, the turnbuckle assembly 104 may function as a control mechanism for controlling the relative position of the inner ring element 124 with respect to the first and second outer ring elements 120, 122. The turnbuckle assembly 104 may generally comprise a first fixation element 180, a second fixation element 182, and a spanning element 184 extending between the first and second fixation elements 180, 182. The spanning element 184 may be configured to rotatably couple with the first and second fixation elements 180, 182 via threading formed within the spanning element 184 and on the first and second fixation elements 180, 182.

Figure 2:
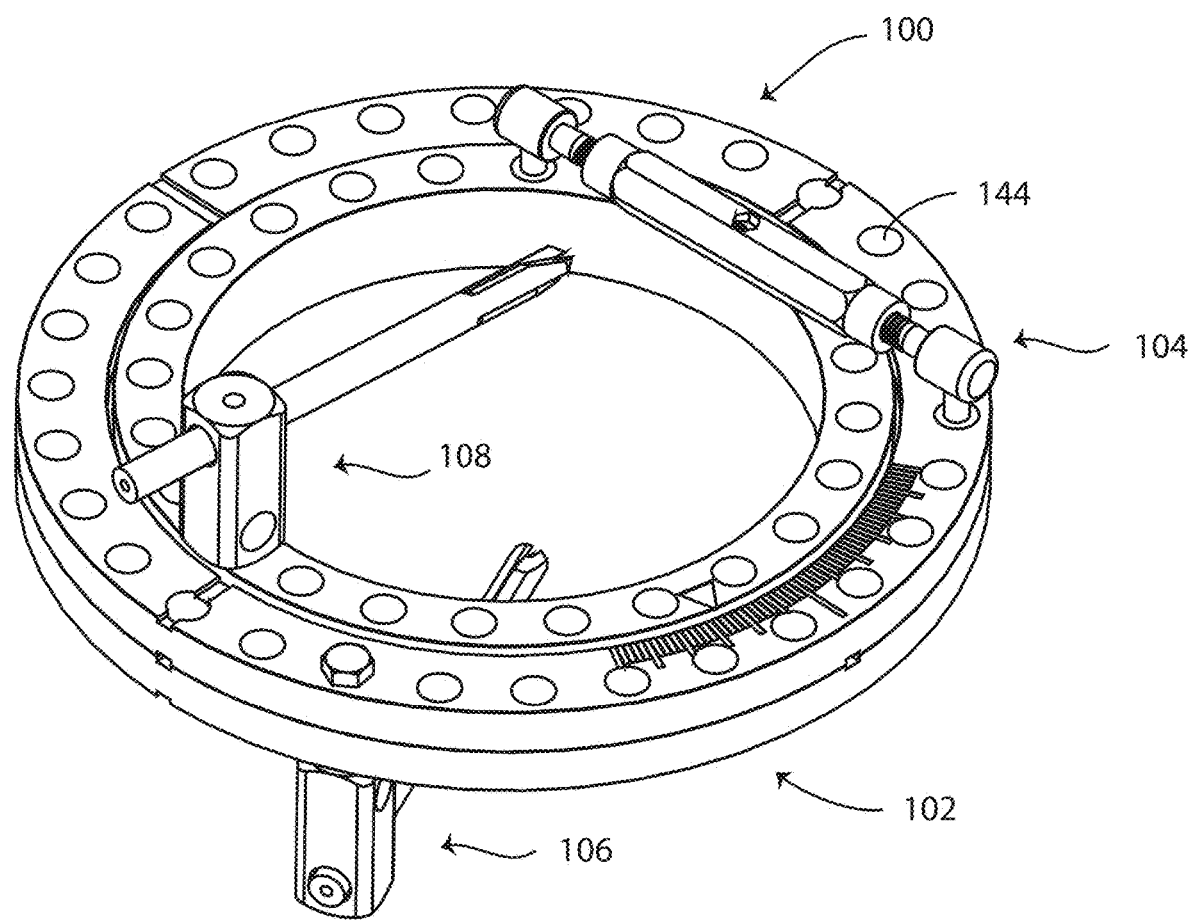
FIG. 2 is a perspective view of an anteversion correction device.

As shown in FIG. 2, the first fixation element 180 may be attached to one of the inner or outer ring elements, and the second fixation element 182 may attached to the other of the inner or outer ring elements. Thus, the first and second fixation elements 180, 182 may be received within the columnar passageways 144 of the first and second outer ring elements 120, 122, and/or within the inner ring apertures 162 of the inner ring element 124 in order to pivotably couple the turnbuckle assembly 104 to the coupled ring assembly 102.

Once the turnbuckle assembly 104 has been pivotably coupled to the coupled ring assembly 102, the effective length of the spanning element 184 of the turnbuckle assembly 104 may be adjusted/increased (for example by rotating the spanning element 184 in a first direction, which may cause the first and second fixation elements 180, 182 to move away from each other), in order to adjust a rotational juxtaposition of the inner and outer ring elements with respect to each other to provide and maintain a corrective torsional force between the first and second fixation pin assemblies 106, 108. However, it will also be understood that any number of different mechanisms are envisioned herein for adjusting the relative positions of the outer and inner ring elements with respect to each other, such as an outrigger mechanism, a locking mechanism, a control mechanism, etc. (not shown). Likewise, the effective length of the spanning element 184 of the turnbuckle assembly 104 may also be adjusted/decreased (for example by rotating the spanning element 184 in a second direction, which may cause the first and second fixation elements 180, 182 to move toward each other), in order to adjust a rotational juxtaposition of the inner and outer ring elements with respect to each other and reduce a corrective torsional force between the first and second fixation pin assemblies 106, 108.

Figure 13A:
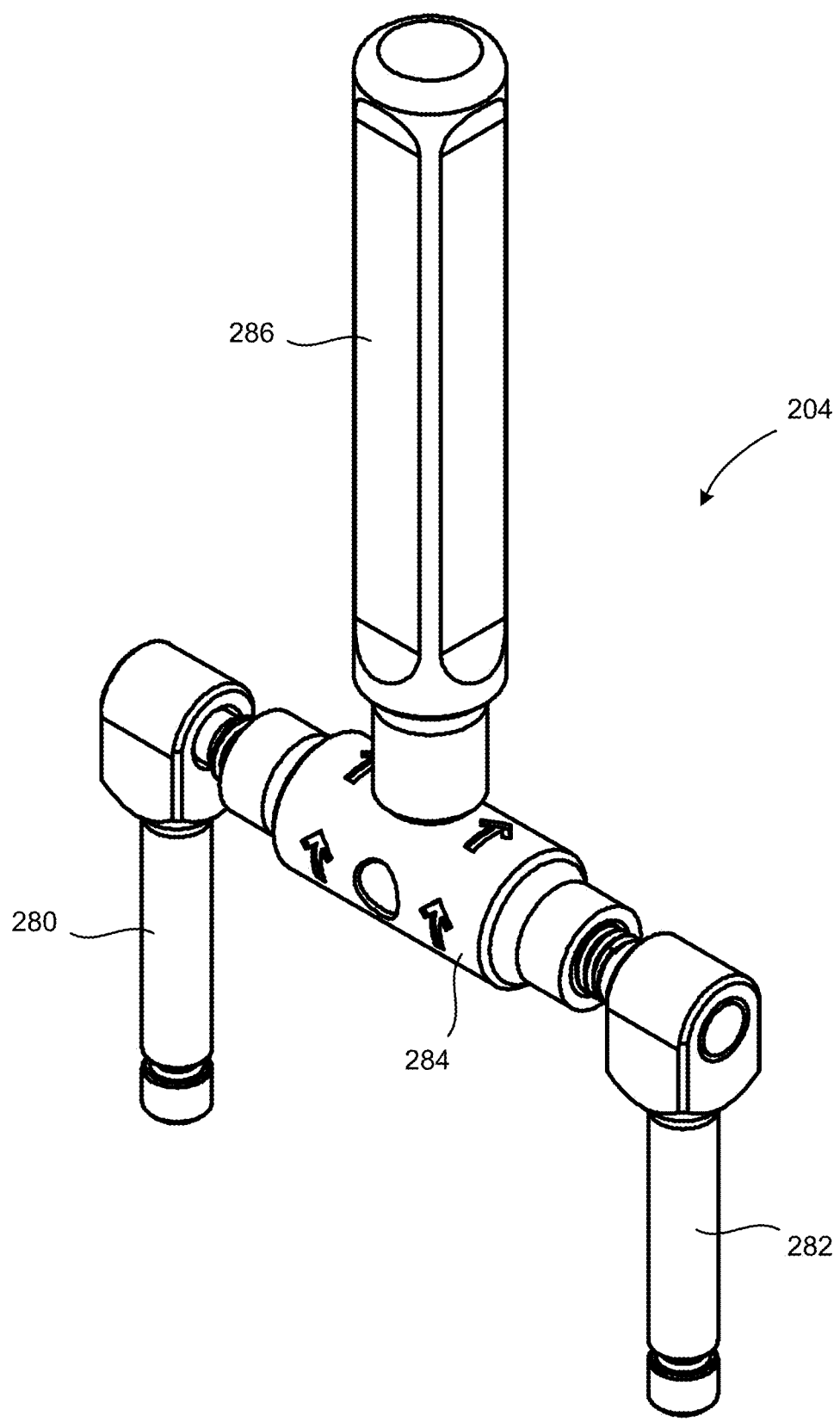
FIG. 13A is a perspective view of an example turnbuckle assembly, according to another embodiment of the present disclosure.
Figure 13B:
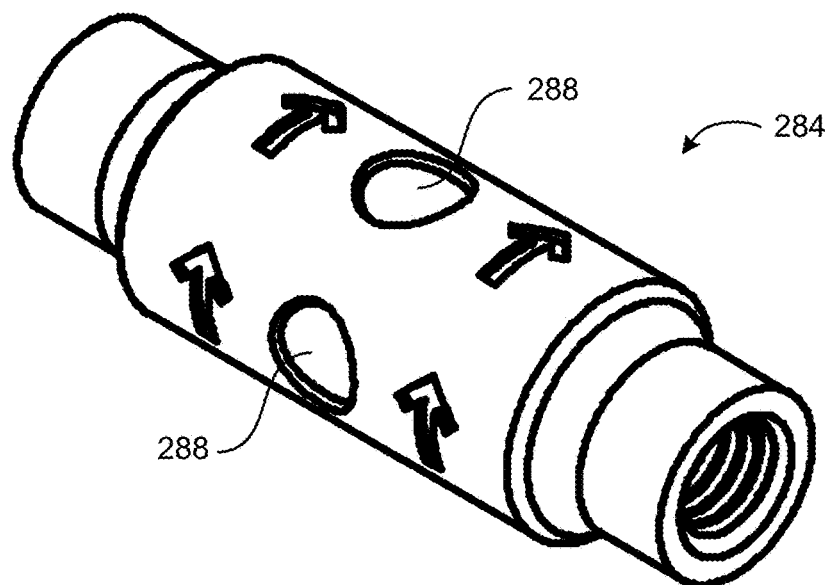
FIG. 13B is a perspective view of a spanning element of the turnbuckle assembly of FIG. 13A.
Figure 13C:
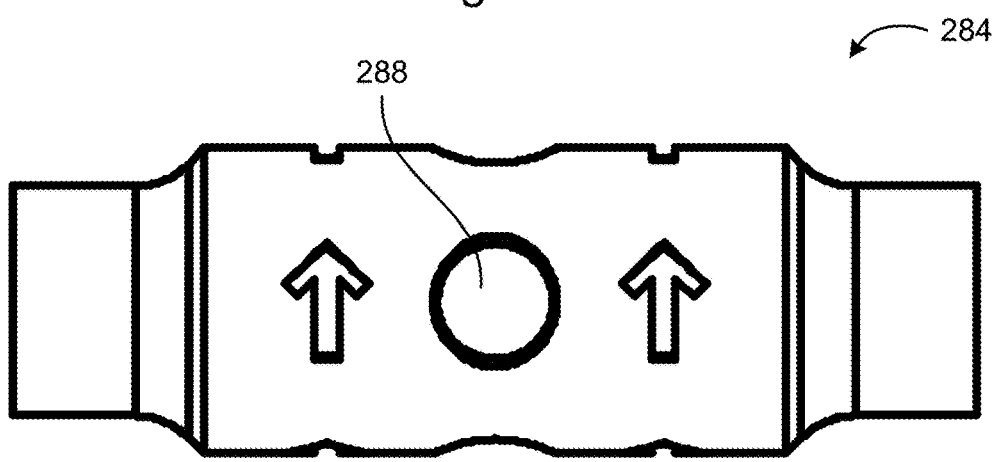
FIG. 13C is a side view of the spanning element of FIG. 13B.
Figure 13D:
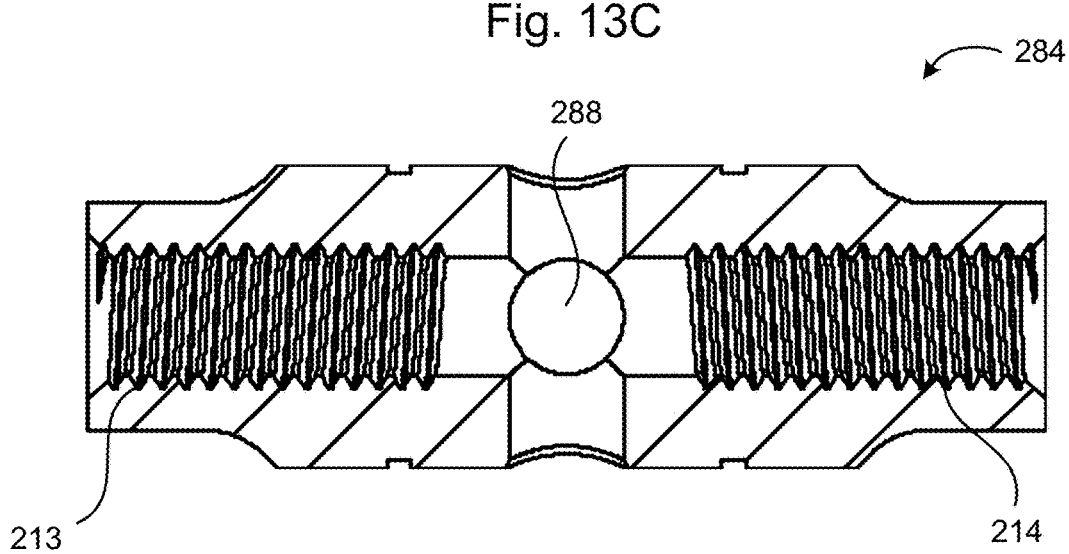
FIG. 13D is a cross-sectional side view of the spanning element of FIG. 13B.
Figure 13E:
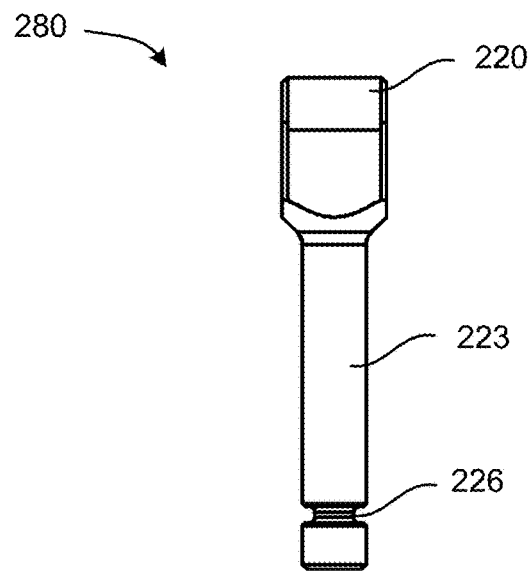
FIG. 13E is a front side view of a fixation element of the turnbuckle assembly of FIG. 13A.
Figure 13F:
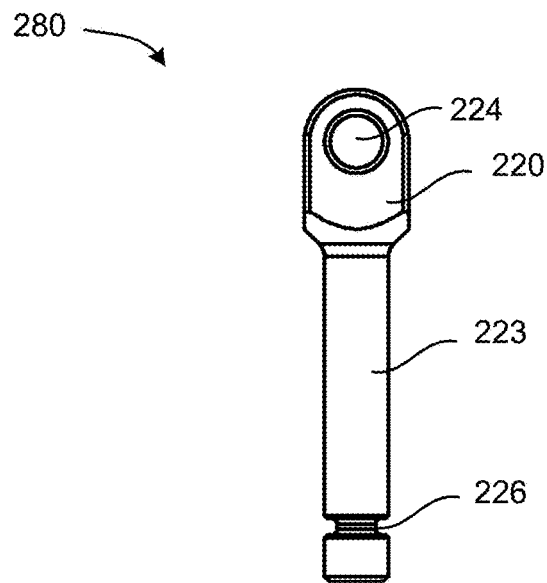
FIG. 13F is a right side view of the fixation element of FIG. 13E.
Figure 13G:
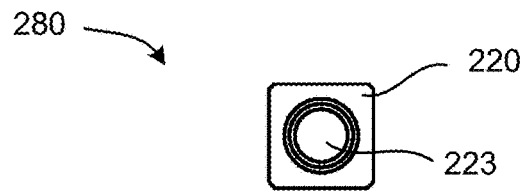
FIG. 13G is an inferior view of the fixation element of FIG. 13E.
Figure 13H:
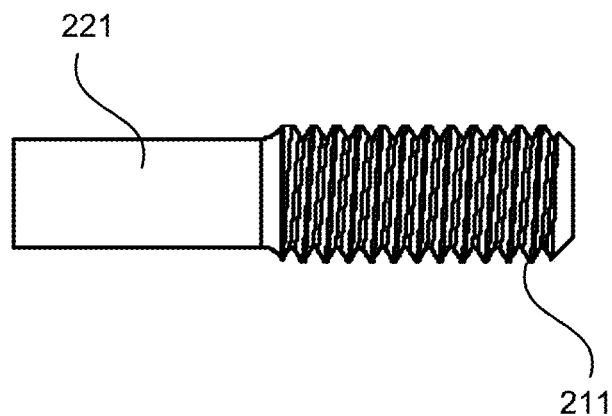
FIG. 13H is a side view of a first fixation element fastener of the turnbuckle assembly of FIG. 13A.
Figure 13I:
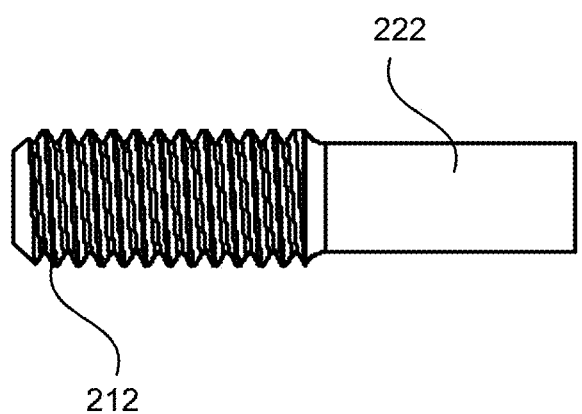
FIG. 13I is a side view of a second fixation element fastener of the turnbuckle assembly of FIG. 13A.
Figure 13J:
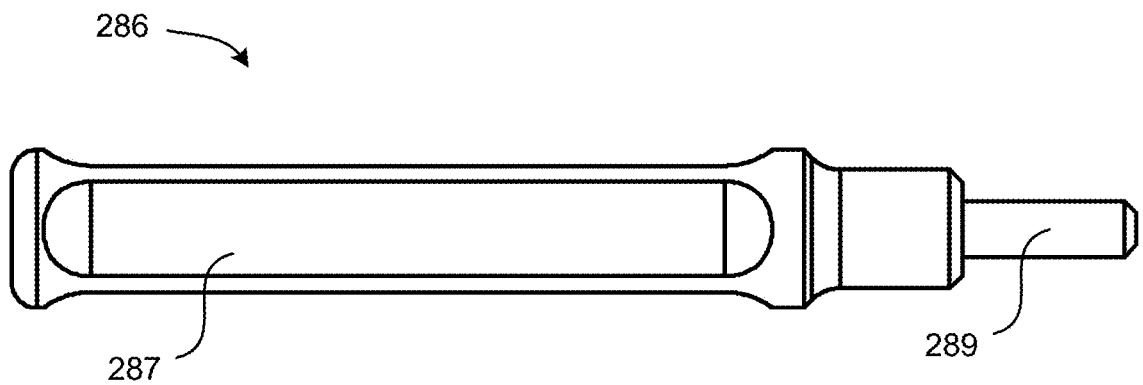
FIG. 13J is a side view of an actuator tool that may be utilized with the turnbuckle assembly of FIG. 13A.

FIGS. 13A-J illustrate a turnbuckle assembly 204, according to another embodiment of the present disclosure, which may also be utilized with the coupled torsion fixators 100, 200 described herein. Specifically, FIG. 13A is a perspective view of the turnbuckle assembly 204; FIG. 13B is a perspective view of a spanning element 284 of the turnbuckle assembly 204; FIG. 13C is a side view of the spanning element 284; FIG. 13D is a cross-sectional side view of the spanning element 284; FIG. 13E is a front side view of a first fixation element 280 of the turnbuckle assembly 204; FIG. 13F is a right side view of the first fixation element 280; FIG. 13G is an inferior view of the first fixation element 280; FIG. 13H is a side view of a first fixation element fastener 221 of the turnbuckle assembly 204; FIG. 13I is a side view of a second fixation element fastener 222 of the turnbuckle assembly 204; and FIG. 13J is a side view of an actuator tool 286 that may be utilized to actuate the spanning element 284 of the turnbuckle assembly 204.

The turnbuckle assembly 204 may likewise function as a control mechanism for controlling the relative position of the first arcuate segment (or first and second outer ring elements 120, 122) with respect to the second arcuate segment (or inner ring element 124). The turnbuckle assembly 204 may generally comprise the first fixation element 280, the second fixation element 282, a first fixation element fastener 221 coupled to the first fixation element 280, a second fixation element fastener 222 coupled to the second fixation element 282, and the spanning element 284 extending between the first and second fixation element fasteners 221, 222.

In at least one embodiment, the first and second fixation elements 280, 282 may be identical. Accordingly, the first fixation element 280 will be described below with the understanding that this description may also apply to the second fixation element 282.

With reference to FIGS. 13E-G, the first fixation element 280 may generally include a first fixation element head 220, a first fixation element aperture 224 formed through the first fixation element head 220, a first fixation element shaft 223, and a first fixation element notch 226. The first fixation element notch 226 may be utilized to couple the first fixation element 280 to the coupled ring assembly 102 (e.g., via a cotter pin (not shown), or the like). The first fixation element fastener 221 may couple with the first fixation element 280 via the first fixation element aperture 224 formed in the first fixation element head 220. However, it will be understood that in other embodiments the first fixation element 280 and the first fixation element fastener 221 may comprise a single monolithic body.

The spanning element 284 may be configured to rotatably couple with the first and second fixation element fasteners 221, 222 via threading formed within the spanning element 284 and on the first and second fixation element fasteners 221, 222. Specifically, the first fixation element fastener 221 may include first threading 211, the second fixation element fastener 222 may include second threading 212, and the spanning element 284 may include third threading 213 configured to engage the first threading 211 of the first fixation element fastener 221, and fourth threading 214 configured to engage the second threading 212 of the second fixation element fastener 222.

Once the turnbuckle assembly 204 has been pivotably coupled to the first arcuate segment (or first and second outer ring elements 120, 122) and the second arcuate segment (or inner ring element 124), the effective length of the spanning element 284 of the turnbuckle assembly 204 may be adjusted/increased (for example by rotating the spanning element 284 in a first direction, which may cause the first and second fixation elements 280, 282 to move away from each other) in order to adjust a rotational juxtaposition of the first and second arcuate segments with respect to each other to provide and maintain a corrective torsional force between the first and second fixation pin assemblies 106, 108. Likewise, the effective length of the spanning element 284 of the turnbuckle assembly 204 may also be adjusted/decreased (for example by rotating the spanning element 284 in a second direction, which may cause the first and second fixation elements 280, 282 to move toward each other), in order to adjust a rotational juxtaposition of the first and second arcuate segments with respect to each other and reduce a corrective torsional force between the first and second fixation pin assemblies 106, 108. The spanning element 284 may be rotated by inserting the actuator tool engagement feature 289 of the actuator tool 286 into one of the spanning element apertures 288, and then applying a force to the handle 287 of the actuator tool 286 in order to rotate the spanning element 284 in either of the first or second directions. In this manner, the turnbuckle assembly 204 (or other control mechanism) can enable fixation of the second arcuate segment in any of a plurality of orientations relative to the first arcuate segment in order to control an orientation of the first pin with respect to the second pin and exert torsional force on an intact bone between a proximal bone segment and a distal bone segment of the intact bone, thereby externally reducing anteversion of the intact bone.

Figure 9:
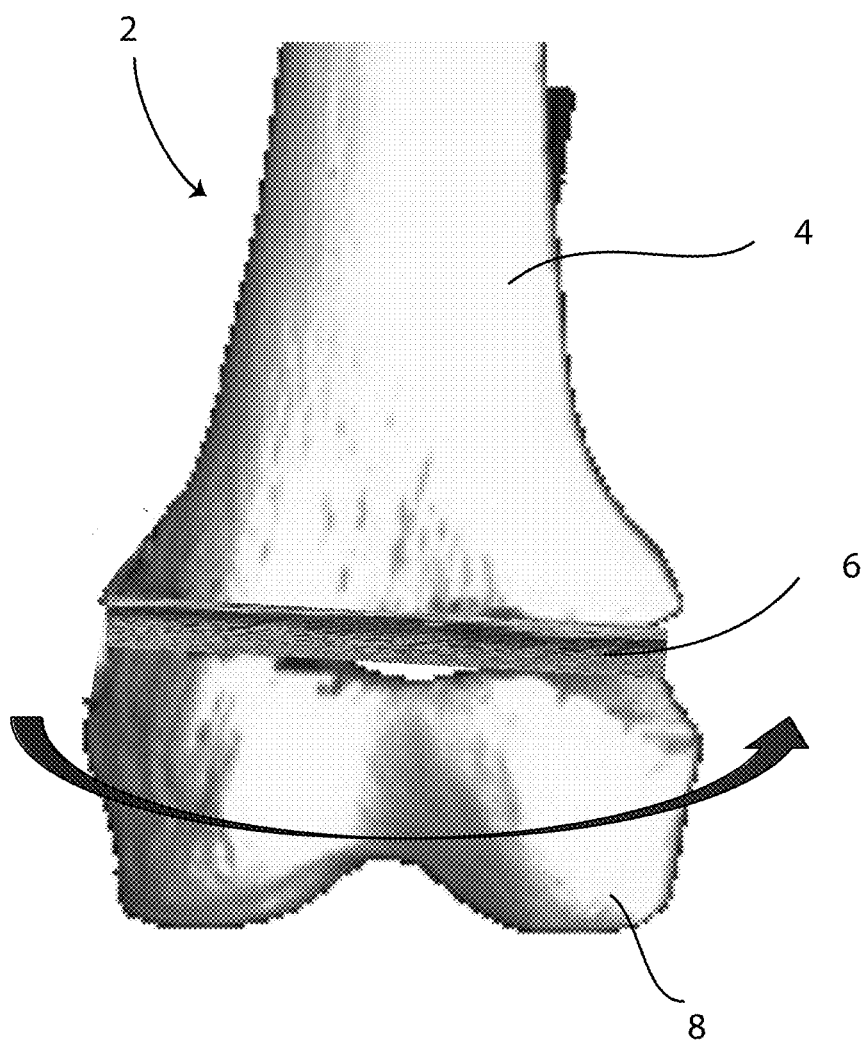
FIG. 9 is an anterior view of a femur distal end, illustrating the location of a physeal growth plate, and including an arrow indicating the direction of torque necessary to correct anteversion of the femur.

In one method of use, the coupled torsional fixator 100 may be positioned to encircle a femur 2 requiring anteversion correction. Prior to positioning the coupled torsional fixator 100, the pins 170 may be drawn out of the way in their respective couplers 172, or removed entirely to allow the femur 2 to pass through the ring assembly bore 126. The coupled torsional fixator 100 may be positioned at a desired location relative to the femur 2, for example at the level of the physis 6, or physeal growth plate, of the femur 2, as illustrated in FIG. 9. With the coupled torsional fixator 100 at the desired position, the pin 170 of the first fixation pin assembly 106 may be percutaneously secured into the femur 2 on one side of the physis 6, for example below the physis 6 in the distal femur 8. The pin 170 of the second fixation pin assembly 108 may be percutaneously secured into the femur 2 on the opposite side of the physis 6, for example above the physis 6 in the femur shaft 4. The pins 170 may be installed at a selected first angle relative to one another from a superior or inferior perspective. In an embodiment, if the amount of correction desired is 30°, the second fixation assembly 108 may be positioned to hold its pin 170 at a 30° angle relative to the first pin 170 of the first fixation pin assembly 106. At this initial position, the pointer 168 on the coupled ring assembly 102 may point at a location relative to the indicia 146 on the coupled ring assembly 102 to indicate an amount of anteversion correction.

The coupled torsional fixator 100 can be gradually adjusted by actuation of the turnbuckle assembly 104, 204 to gradually increase anteversion correction over time. The spanning element 184, 284 may be rotated to adjust the length of the turnbuckle assembly 104, 204 and thus rotate the first arcuate segment or first and second outer ring elements 120, 122 relative to the second arcuate segment or inner ring element 124. This will also adjust a distance/angle between the first and second fixation pin assemblies 106, 108 and their respective pins 170. In doing so, the distal femur 8 may be gradually twisted relative to the femur shaft 4 to correct anteversion.

In an embodiment of the method, the rate of anteversion correction may be 1 degree per day. In another embodiment of the method, the rate of anteversion correction may be less than 1 degree per day. In yet another embodiment of the method, the rate may be more than 1 degree per day.

The turnbuckle assembly 104, 204 may be actuated more than once a day to attain anteversion correction. In an embodiment, the turnbuckle assembly 104, 204 may be actuated three times a day. In other embodiments, the rate of anteversion correction that is implemented may vary from day to day.

In some embodiments of the method, the initial angle of the pins 170 relative to one another may vary, and the pins 170 need not be parallel to one another at the completion of the derotation process, or at any point during the derotation process. As anteversion correction proceeds, the pins 170 may gradually move toward one another until they reach a selected second angle, in at least some embodiments. In an embodiment, the selected second angle may be 0°, such that the pins 170 are vertically aligned from a superior or inferior perspective and they are parallel, or substantially parallel, relative to one another. At this juncture, the pointer 168 may be pointing at the zero degree indicator(s) of the indicia 146. After correction of the anteversion, the torsional fixator 100 may be removed from the patient.

Figure 12:
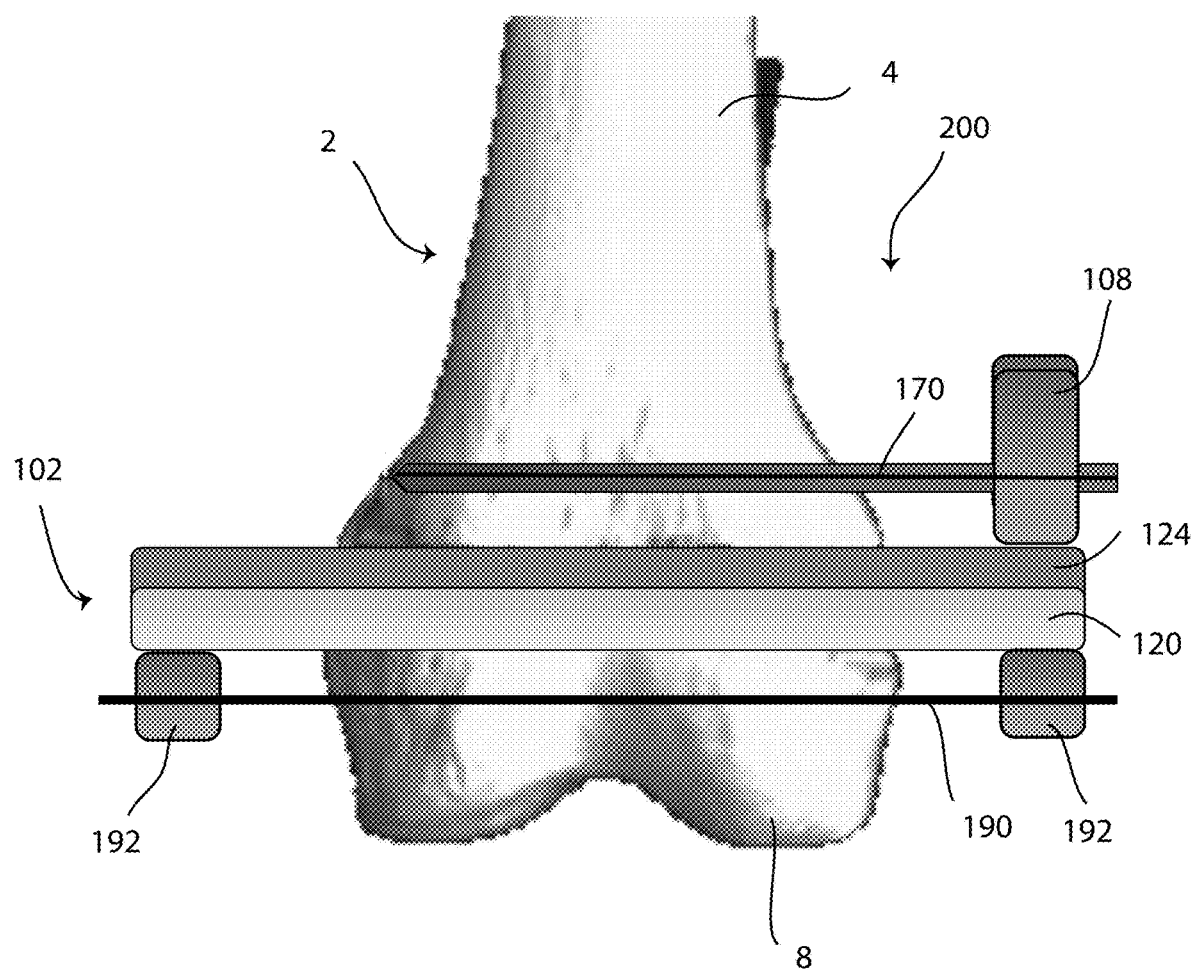
FIG. 12 is an anterior view of the femur and the anteversion correction device of FIG. 10, after correction of anteversion in the femur.

Referring to FIGS. 10-12, in an alternate embodiment of the disclosure, at least one of the first and second pins 170 may comprise one or more wires 190 that are secured between two opposing couplers 192 that are positioned on opposite sides of the coupled ring assembly 102. For example, the two opposing couplers 192 may be coupled on opposite sides of the first arcuate segment (or inner ring element 124), or they may be coupled on opposite sides of the second arcuate segment (or first and second outer ring elements 120, 122), or they may be coupled on opposite sides of the outer ring assembly 103, etc. In this manner, the one or more wires 190 may extend across the coupled ring assembly 102 between the two opposing couplers 192 which are attached to the coupled ring assembly 102.

FIGS. 10-12 illustrate one example of such an alternate embodiment, including a coupled torsional fixator 200 secured to the femur 2. One or more wires 190 may extend through the femur 2 below the physis and may be secured to the second arcuate segment or inner ring element 124, as shown in this example. A pin 170 may also be secured to the femur 2 above the physis and the pin 170 may be secured to the first arcuate segment or first outer ring element 120. The turnbuckle assembly 104 may control the relative movement between the inner ring element 124 and the first outer ring element 120. In FIG. 11, correction of the anteversion has almost been completed, with about one degree of correction remaining. In FIG. 12, correction of the anteversion has been completed, and the pin 170 is shown parallel with the wires 190.

Figure 14:
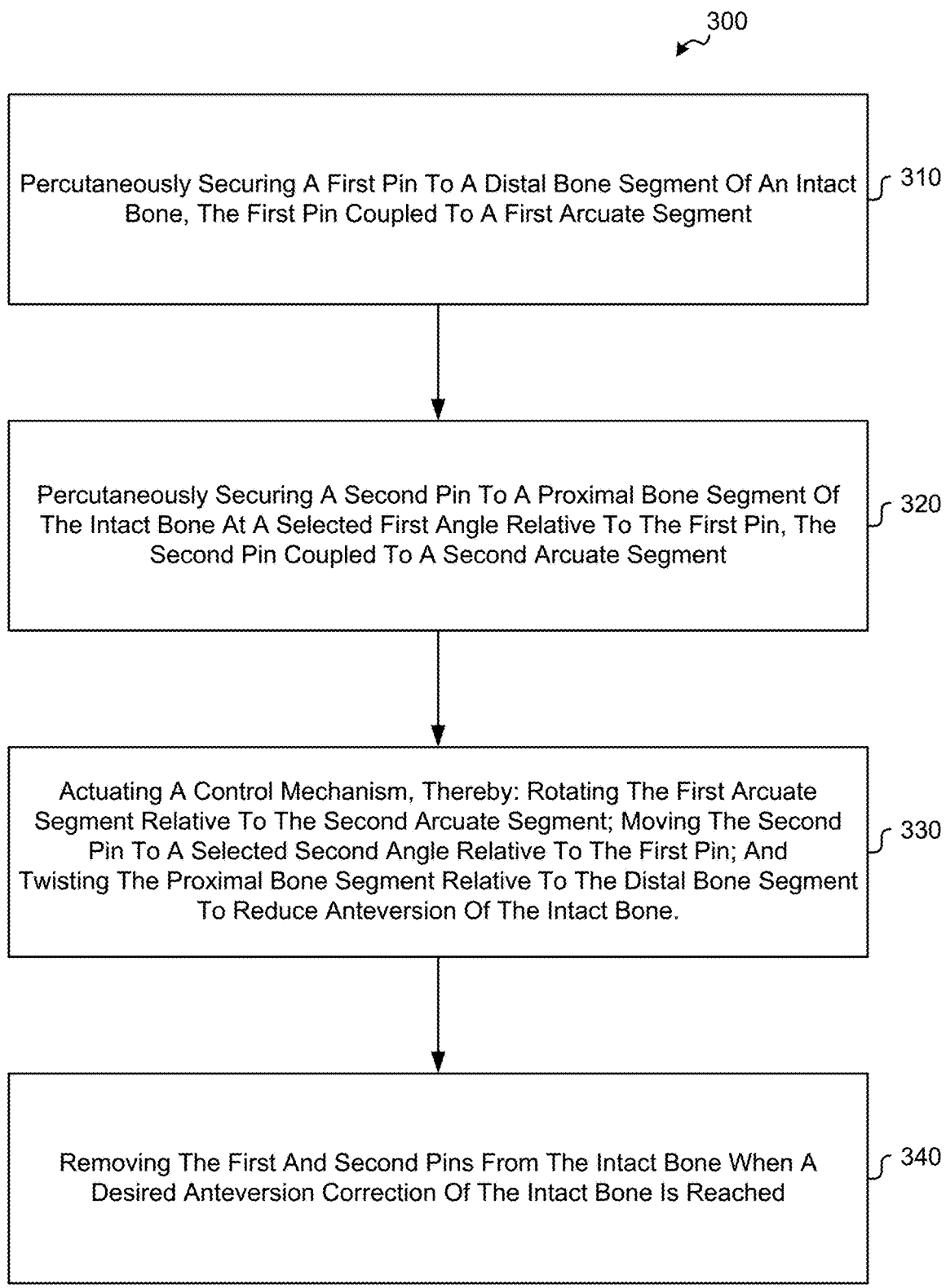
FIG. 14 is a flow chart of a method for external anteversion correction of an intact bone, according to an embodiment of the present disclosure.

FIG. 14 illustrates a flow chart of a method 300 for external anteversion correction of an intact bone, according to an embodiment of the present disclosure. In general, the method 300 may utilize any of the devices or device components described herein, in any combination or configuration. In one example, the method 300 may utilize a device comprising a first arcuate segment and a second arcuate segment rotatably coupled together, a first pin coupled to the first arcuate segment, a second pin coupled to the second arcuate segment, and a control mechanism coupled to the first and second arcuate segment.

The method may begin with a step 310 in which a first pin may be percutaneously secured to a distal bone segment of an intact bone. The first pin may also be coupled to the first arcuate segment, either directly, or indirectly via a first fixation assembly.

Once the first pin has been percutaneously secured to the distal bone segment of the intact bone, the method 300 may proceed to a step 320 in which a second pin may be percutaneously secured to a proximal bone segment of the intact bone at a selected first angle relative to the first pin. The second pin may also be coupled to the second arcuate segment, either directly, or indirectly via a second fixation assembly. Moreover, in some embodiments the first arcuate segment may comprise an outer ring and the second arcuate segment may comprise an inner ring concentrically and rotatably coupled to the outer ring.

Once the second pin has been percutaneously secured to the proximal bone segment of the intact bone, the method 300 may proceed to a step 330 in which the control mechanism may be actuated, thereby: (1) rotating the first arcuate segment relative to the second arcuate segment; (2) moving the second pin to a selected second angle relative to the first pin; and; (3) twisting the proximal bone segment relative to the distal bone segment to reduce anteversion of the intact bone.

In some embodiments, actuating the control mechanism may further comprise incrementally actuating the control mechanism over a period of time, thereby: (1) rotating the inner ring relative to the outer ring to a plurality of different positions; (2) moving the second pin to a plurality of different angles relative to the first pin; and (3) gradually twisting the proximal bone segment relative to the distal bone segment to reduce anteversion of the intact bone over the period of time.

In some embodiments, actuating the control mechanism may further comprise rotating at least a portion of the control mechanism, thereby: (1) increasing a length of the control mechanism; (2) rotating the inner ring relative to the outer ring; (3) moving the second pin to a selected second angle relative to the first pin; and (4) twisting the proximal bone segment relative to the distal bone segment to reduce anteversion of the intact bone.

In some embodiments, rotating the at least a portion of the control mechanism in a first direction increases the length of the control mechanism, and rotating the at least a portion of the control mechanism in a second direction decreases the length of the control mechanism.

Once the control mechanism has been actuated, the method 300 may proceed to a step 340 in which the first and second pins may be removed from the intact bone when a desired amount of anteversion correction has been reached, and the method 300 may end.

Any methods disclosed herein comprise one or more steps or actions for performing the described method. One or more of the method steps and/or actions may be omitted from any of the methods disclosed herein. Moreover, any of the method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

As defined herein, "substantially equal to" means "equal to," or within about a + or −10% relative variance from one another.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the systems, methods, and devices disclosed herein.

What is claimed is:

1. A method for external anteversion correction of an intact bone through use of a device comprising a first arcuate segment and a second arcuate segment rotatably coupled together, a first pin coupled to the first arcuate segment, a second pin coupled to the second arcuate segment, and a control mechanism coupled to the first and second arcuate segments, the method comprising:
   percutaneously securing the first pin to a distal bone segment of the intact bone;
   percutaneously securing the second pin to a proximal bone segment of the intact bone at a selected first angle relative to the first pin; and
   actuating the control mechanism, thereby:
      rotating the first arcuate segment relative to the second arcuate segment;
      moving the second pin to a selected second angle relative to the first pin; and
      twisting the proximal bone segment relative to the distal bone segment to reduce anteversion of the intact bone.

2. The method of claim 1, wherein:
   the first arcuate segment comprises an outer ring; and
   the second arcuate segment comprises an inner ring, the inner ring concentrically and rotatably coupled to the outer ring.

3. The method of claim 2, wherein actuating the control mechanism further comprises:
   incrementally actuating the control mechanism over a period of time, thereby:
      rotating the inner ring relative to the outer ring to a plurality of different positions;
      moving the second pin to a plurality of different angles relative to the first pin; and
      gradually twisting the proximal bone segment relative to the distal bone segment to reduce anteversion of the intact bone over the period of time.

4. The method of claim 1, further comprising:
   removing the first and second pins from the intact bone when a desired amount of anteversion correction is reached.

5. The method of claim 2, wherein actuating the control mechanism comprises:
   rotating at least a portion of the control mechanism, thereby:
      increasing a length of the control mechanism;
      rotating the inner ring relative to the outer ring;
      moving the second pin to the selected second angle relative to the first pin; and
      twisting the proximal bone segment relative to the distal bone segment to reduce anteversion of the intact bone.

6. The method of claim 5, wherein:
   rotating the at least a portion of the control mechanism in a first direction increases the length of the control mechanism; and
   rotating the at least a portion of the control mechanism in a second direction decreases the length of the control mechanism.

7. The method of claim 5, wherein the control mechanism comprises:
   a turnbuckle assembly comprising:
      a first fixation element configured to pivotally couple with the outer ring;
      a second fixation element configured to pivotally couple with the inner ring; and
      a spanning element configured to rotatably couple with the first fixation element and the second fixation element;
   wherein actuating the control mechanism comprises:
      rotating the spanning element, thereby:
         increasing the length of the control mechanism;
         rotating the inner ring relative to the outer ring;
         moving the second pin to the selected second angle relative to the first pin; and
         twisting the proximal bone segment relative to the distal bone segment to reduce anteversion of the intact bone.

* * * * *